United States Patent [19]

Sirén

[11] Patent Number: 5,407,924
[45] Date of Patent: Apr. 18, 1995

[54] METHOD OF TREATING PAIN USING INOSITOL TRIPHOSPHATE

[75] Inventor: Matti Sirén, Helsingfors, Finland

[73] Assignee: Perstorp AB, Perstorp, Sweden

[21] Appl. No.: 160,555

[22] Filed: Dec. 1, 1993

Related U.S. Application Data

[63] Continuation-in-part of Ser. No. 900,129, Jun. 18, 1992, Pat. No. 5,330,979, which is a continuation-in-part of Ser. No. 580,661, Sep. 11, 1990, Pat. No. 5,128,332, which is a continuation-in-part of Ser. No. 492,740, Mar. 13, 1990, Pat. No. 5,015,634, which is a continuation-in-part of Ser. No. 367,968, Jun. 19, 1989, Pat. No. 5,051,411, which is a continuation-in-part of Ser. No. 251,566, Sep. 30, 1988, Pat. No. 5,023,248, which is a continuation-in-part of Ser. No. 173,985, Mar. 28, 1988, Pat. No. 5,019,566, which is a continuation-in-part of Ser. No. 38,230, Apr. 14, 1987, abandoned, which is a continuation-in-part of Ser. No. 15,679, Feb. 17, 1987, Pat. No. 4,797,390, which is a continuation-in-part of Ser. No. 788,801, Oct. 18, 1985, Pat. No. 4,735,936.

[30] Foreign Application Priority Data

Oct. 23, 1984 [SE] Sweden ............................... 8405295
Apr. 16, 1986 [SE] Sweden ............................... 8601709

[51] Int. Cl.$^6$ ............................................. A61K 31/66
[52] U.S. Cl. ..................................................... 514/103
[58] Field of Search ........................................ 514/103

[56] References Cited

U.S. PATENT DOCUMENTS

| | | | |
|---|---|---|---|
| 4,735,902 | 4/1988 | Siren | 435/188 |
| 4,735,936 | 4/1988 | Siren | 514/199 |
| 4,777,134 | 10/1988 | Siren | 435/155 |
| 4,793,945 | 12/1988 | Siren | 252/400.2 |
| 4,797,390 | 1/1989 | Siren | 514/103 |

*Primary Examiner*—Raymond Henley, III
*Assistant Examiner*—T. J. Criares
*Attorney, Agent, or Firm*—Scully, Scott, Murphy & Presser

[57] ABSTRACT

A method of preventing or alleviating pain by administering to a human or other mammal in need thereof of a pain preventing or alleviating effective amount of a pharmaceutical composition comprising at least one specific isomer of inositol triphosphate.

5 Claims, No Drawings

1

METHOD OF TREATING PAIN USING INOSITOL TRIPHOSPHATE

REFERENCE TO RELATED APPLICATIONS

This is a continuation-in-part of application, Ser. No. 900,129, filed Jun. 18, 1992, now U.S. Pat. No. 5,330,979, which is a continuation-in-part of application, Ser. No. 580,661 filed Sept. 11, 1990, now U.S. Pat. No. 5,128,332, which is a continuation-in-part of application, Serial No. 492,740, filed Mar. 13, 1990, now U.S. Pat. No. 5,015,634, which is a continuation-in-part of application, Ser. No. 367,968, filed Jun. 19, 1989, now U.S. Pat. No. 5,051,411, which is a continuation-in-part of application, Ser. No. 251,566, filed Sept. 30, 1988, now U.S. Pat. No. 5,023,248, which is a continuation-in-part of application, Ser. No. 173,985, filed Mar. 28, 1988, now U.S. Pat. No. 5,019,566, which is a continuation-in-part of application, Ser. No. 038,230, filed Apr. 14, 1987, now abandoned, which is a continuation-in-part of application, Ser. No. 015,679, filed Feb. 17, 1987, now U.S. Pat. No. 4,797,390, which is a continuation-in-part of application, Ser. No. 788,801, filed Oct. 18, 1985, now U.S. Pat. No. 4,735,936.

FIELD OF INVENTION

The present invention relates to a method of preventing or alleviating different conditions in the body by administering thereto a pharmaceutical composition comprising an amount of at least one isomer of inositoltrisphosphate sufficient to obtain said prevention or alleviation.

Many diseases and medical procedures are characterized by the sense of pain in different ways for the patient. For example during and after surgical operations the manifestation of pain is high. The same is true for many disorders related to trauma. Thus e.g. burn patients suffer great pain directly after an accident but also during the recovery period. Pain is also mainfested in most inflammatory conditions and in association tumour-related diseases or treatment of those. Different therapeutics are used in order to achieve an analgetic or anaesthetic effect. Various types of local anaesthetics are utilized to abolish the sensation of pain to a limited area of the body around the site of its application. Other drugs such as opioids, for example morphine, are used for reducing severe pain related to surgical operations. Another type of pharmaceuticals used to reduce pain are sedative agents such as barbiturates and benzodiazepines. Many of these drugs have side effects such as depressant action on respiration and circulation and are producing nausea and vomiting, which limit their use to many groups of patients. Furthermore many of the used drugs give hypnotic effects which are undesirable for the patient. Nonsteroidal anti-inflammatory drugs are used to treat pain and inflammation. This class of compounds works by preventing the synthesis of prostaglandins and side-effects such as damage to the gastic mucosa often appear.

SUMMARY OF THE INVENTION

According to the present invention it has surprisingly become possible to overcome and reduce the above mentioned disorders as a method of preventing or alleviating these conditions has been brought about. At said method a pharmaceutical composition comprising at least one isomer of inositoltrisphosphate (IP$_3$) sufficient to obtain said prevention or alleviation is administered to a human or an animal.

Preferred embodiments of the invention relate to a method of preventing or alleviating pain by administering a pharmaceutical composition comprising an amount of at least one specific isomer of IP$_3$ sufficient to obtain said prevention or alleviation to a human or an animal.

The composition can be used for example in the following conditions in order to reduce pain and be effective as an analgesic:

Tissue damage induced mechanically or chemically such as burns, trauma i.e. wounds or injuries caused by physical damage.

Injuries following surgery or operations.

Conditions related to tumours.

Inflammatory conditions such as joint inflammations.

The composition can also be effective in other disorders or conditions where reduction of pain is desirable.

The medicament exerts significant analgesic effects without showing any side-effects and without any sedative effects which is very beneficial for the patient.

From the European Patent No 179439 a pharmaceutical composition comprising as a pharmaceutically active ingredient at least one isomer of inositoltrisphosphate is known. In said patent the effect of this pharmaceutical composition is shown for different areas, such as platelet aggregation.

The production of IP$_3$ and the isolation of the different isomers thereof are disclosed in the U.S. Pat. No. 4,777,134. The IP$_3$ isomers can also be produced by synthetic methods, chemically or enzymatically, starting with e.g. inositol and a phosphorus source. Furthermore, microbiological production methods including hybrid DNA-techniques of IP$_3$ are also suitable.

The structure of IP$_3$ and the different isomers thereof are disclosed in the U.S. Pat. No 4,735,936 and the U.S. Pat. No. 4,797,390.

It is suitable that the composition used according to the invention exists in unit dosage form. Tablets, granules or capsules are suitable administration forms for such unit dosage. Furthermore, tablets and granules can easily be surface treated such as to provide an enteric coating to prevent an uncontrolled hydrolysis in the stomach and to bring about a desired absorption in the intestine. Other suitable administration forms are slow release and transdermal administration nasal, rectal, intraarticular, topical, intraperitoneal and subcutaneous administration. A usual pharmaceutically acceptable additive, excipient and/or carrier can be included in the medicament. The tablets or granules can also contain a disintegrant which causes the tablets or the granules, respectively, to disintegrate easily in the intestine. In certain cases, especially in acute situations, it is preferable to use the unit dosage in the form of a solution for intravenous administration. In other situations suspensions comprising the compound can be preferably used as administration form.

The pharmaceutical composition can also consist as such of IP$_3$ solely without any additive, excipient or carrier.

If desired, the composition can be free of other inositol phosphates, IP$_1$, IP$_2$, IP$_4$, IP$_5$ and IP$_6$. Accordingly, the mixture of IP$_3$ isomers can have a purity of 90-100% or preferably 95-100%.

Alternatively, the pharmaceutical composition used in the method can consist of or comprise one or more specific IP$_3$ isomers, each present in substantially pure form. Thus, the different isomers can be isolated from each other in substantially pure form, which means that they have a purity of 80–100 %, such as 82–100 % or 85–100 %, preferably 90–100 %. Since the isomers can be produced in pure form they can be mixed in any proportion, of course. The composition can consist of $IP_3$, wherein said $IP_3$ is provided by at least one of $IP_6$, $IP_5$ or $IP_4$ and a degradative substance such as an enzyme suitable to form $IP_3$.

It is in most cases suitable that the $IP_3$-isomer or isomers in the composition used in the method according to the invention are present in salt form in order not to affect the mineral balance negatively. The salt should preferably consist of a sodium, potassium, calcium, zinc or magnesium salt or a mixture of two or more of these salts.

For the above mentioned reasons it is also an advantage if the compositions contains a surplus or an extra addition of at least one pharmaceutically acceptable salt of calcium, zinc or magnesium with a mineral acid or organic acid. This is especially valuable for elderly persons who are often deficient in these minerals.

For administration to human patients appropriate dosages can routinely be determined by those skilled in this art by extension of the results obtained in animals at various dosages. The preferred dosage for humans falls within the range of 0.1 to 1000 mg, especially 0.1–200 mg $IP_3$/day/kg body weight.

The pharmaceutical composition used in the method according to the invention usually contains 0.01–1.5 g, such as 0.05–1.3 g or preferably 0.1–1 g of $IP_3$ per unit dosage.

The composition used according to the present invention contains at least one, sometimes two or more of the following substances, which correspond to the essential $IP_3$-isomer or isomers mentioned above:

D-myo-inositol-1.2.6-trisphosphate of the formula

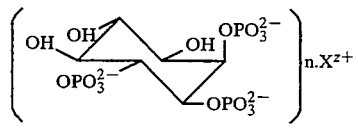

where X is hydrogen, at least one univalent, divalent or multivalent cation, or a mixture thereof, n is the number of ions, and z is the charge of the respective ion;

Myo-inositol-1.2.3-trisphosphate of the formula

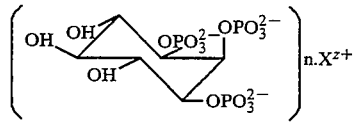

where X, n and z have the above mentioned meaning;

L-myo-inositol-1.3.4-trisphosphate of the formula

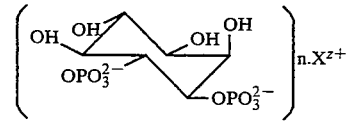

where X, n and z have the above mentioned meaning.

In each of the above formulas n ranges between 6 to 1 inclusive and z ranges from 1 to 6 inclusive. Preferably, n is between 3 to 6 inclusive and z is 3, 2 or 1. Of the above isomers D-myo-inositol-1.2.6-trisphosphate is preferred.

Other inositol trisphoshate isomers that may be utilized in the present invention as the active $IP_3$ ingredient in the composition have the structural formula

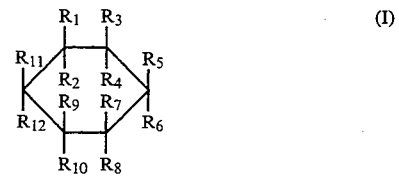

One group of inositol trisphosphate compounds is defined by the structural formula (I) where three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen.

Another group of inositol trisphosphates is defined by the structural formula (I) where three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen.

Still another group of inositol trisphosphates is defined by the structural formula (I) where three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen.

Yet another group of inositol trisphosphates is defined by the structural formula (I) where three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen.

Still yet another group of inositol trisphosphates is defined by the structural formula (I) where three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen.

Even still another group of inositol trisphosphates is defined by the structural formula (I) where three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen.

Even yet another group of inositol trisphosphates is defined by the structural formula (I) where three of $R_1$, $R_3$, $R_5$, $R_8$, $R_{10}$ and $R_{11}$ are hydroxyl and the remaining three are phosphate and $R_2$, $R_4$, $R_6$, $R_7$, $R_9$ and $R_{12}$ are hydrogen.

Finally, another group of inositol trisphosphates is defined by the structural formula (I) where three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

Particular inositol trisphosphate compounds within the contemplation of the above formula include compounds having the structural formula (I) where $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen;

$R_1$, $R_{10}$ and $R_{11}$ are phosphate, $R_3$, $R_5$ and $R_7$ are hydroxyl and $R_2$, $R_4$, $R_6$, $R_8$, $R_9$ and $R_{12}$ are hydrogen;

$R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen;

$R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen;

$R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen;

$R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen;

$R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen;

$R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen;

$R_3$, $R_5$ and $R_8$ are phosphate, $R_1$, $R_{10}$ and $R_{12}$ are hydroxyl and $R_2$, $R_4$, $R_6$, $R_7$, $R_9$ and $R_{11}$ are hydrogen;

$R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen;

$R_1$, $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_8$ are phosphate, $R_3$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_{12}$ are phosphate, $R_3$, $R_8$ and $R_{10}$ are hydroxyl and $R_2$, $R_4$, $R_6$, $R_7$, $R_9$ and $R_{11}$ are hydrogen;

$R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen;

$R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen;

$R_4$, $R_5$ and $R_8$ are phosphate, $R_1$, $R_9$ and $R_{12}$ are hydroxyl and $R_2$, $R_3$, $R_6$, $R_7$, $R_{10}$ and $R_{11}$ are hydrogen;

$R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_7$, $R_9$ and $R_{11}$ are hydroxyl and $R_2$, $R_4$, $R_6$, $R_8$, $R_{10}$ and $R_{12}$ are hydrogen;

$R_1$, $R_3$ and $R_{12}$ are phosphate, $R_5$, $R_8$ and $R_9$ are hydroxyl and $R_2$, $R_4$, $R_6$, $R_7$, $R_{10}$ and $R_{11}$ are hydrogen;

$R_1$, $R_3$ and $R_8$ are phosphate, $R_5$, $R_9$ and $R_{12}$ are hydroxyl and $R_2$, $R_4$, $R_6$, $R_7$, $R_{10}$ and $R_{11}$ are hydrogen;

$R_3$, $R_5$ and $R_{12}$ are phosphate, $R_1$, $R_8$ and $R_9$ are hydroxyl and $R_2$, $R_4$, $R_6$, $R_7$, $R_{10}$ and $R_{11}$ are hydrogen;

$R_1$, $R_5$ and $R_9$ are phosphate, $R_3$, $R_8$ and $R_{12}$ are hydroxyl and $R_2$, $R_4$, $R_6$, $R_7$, $R_{10}$ and $R_{11}$ are hydrogen;

$R_1$, $R_5$ and $R_{12}$ are phosphate, $R_3$, $R_8$ and $R_9$ are hydroxyl and $R_2$, $R_4$, $R_6$, $R_7$, $R_{10}$ and $R_{11}$ are hydrogen;

$R_1$, $R_3$ and $R_9$ are phosphate, $R_5$, $R_8$ and $R_{12}$ are hydroxyl and $R_2$, $R_4$, $R_6$, $R_7$, $R_{10}$ and $R_{11}$ are hydrogen;

$R_3$, $R_5$ and $R_9$ are phosphate, $R_1$, $R_8$ and $R_{12}$ are hydroxyl and $R_2$, $R_4$, $R_6$, $R_7$, $R_{10}$ and $R_{11}$ are hydrogen;

$R_5$, $R_9$ and $R_{12}$ are phosphate, $R_1$, $R_3$ and $R_8$ are hydroxyl and $R_2$, $R_4$, $R_6$, $R_7$, $R_{10}$ and $R_{11}$ are hydrogen;

$R_1$, $R_8$ and $R_9$ are phosphate, $R_3$, $R_5$ and $R_{12}$ are hydroxyl and $R_2$, $R_4$, $R_6$, $R_7$, $R_{10}$ and $R_{11}$ are hydrogen;

$R_1$, $R_8$ and $R_{12}$ are phosphate, $R_3$, $R_5$ and $R_9$ are hydroxyl and $R_2$, $R_4$, $R_6$, $R_7$, $R_{10}$ and $R_{11}$ are hydrogen;

$R_5$, $R_8$ and $R_{12}$ are phosphate, $R_1$, $R_3$ and $R_9$ are hydroxyl and $R_2$, $R_4$, $R_6$, $R_7$, $R_{10}$ and $R_{11}$ are hydrogen;

$R_1$, $R_9$ and $R_{12}$ are phosphate, $R_3$, $R_5$ and $R_8$ are hydroxyl and $R_2$, $R_4$, $R_6$, $R_7$, $R_{10}$ and $R_{11}$ are hydrogen;

$R_5$, $R_8$ and $R_9$ are phosphate, $R_1$, $R_3$ and $R_{12}$ are hydroxyl and $R_2$, $R_4$, $R_6$, $R_7$, $R_{10}$ and $R_{11}$ are hydrogen;

$R_3$, $R_8$ and $R_9$ are phosphate, $R_1$, $R_5$ and $R_{12}$ are hydroxyl and $R_2$, $R_4$, $R_6$, $R_7$, $R_{10}$ and $R_{11}$ are hydrogen;

$R_3$, $R_9$ and $R_{12}$ are phosphate, $R_1$, $R_5$ and $R_8$ are hydroxyl and $R_2$, $R_4$, $R_6$, $R_7$, $R_{10}$ and $R_{11}$ are hydrogen;

$R_3$, $R_8$ and $R_{12}$ are phosphate, $R_1$, $R_5$ and $R_9$ are hydroxyl and $R_2$, $R_4$, $R_6$, $R_7$, $R_{10}$ and $R_{11}$ are hydrogen; and $R_8$, $R_9$ and $R_{12}$ are phosphate, $R_1$, $R_3$ and $R_5$ are hydroxyl and $R_2$, $R_4$, $R_6$, $R_7$, $R_{10}$ and $R_{11}$ are hydrogen.

The above formula describes specific isomers of inositol trisphosphate where the inositol is selected from the group myoinositol, cisinositol, epiinositol, alloinositol, neoinositol, mucoinositol, chiroinositol and scylloinositol.

The invention will be further explained in the following examples where Example 1–3 demonstrate the effect of $IP_3$ to reduce pain in different conditions and where Example 4 shows the manufacturing of a solution of $IP_3$ for intravenous administration.

Example 1

Six patients having disordered gall-bladder (cholecystectomized patients) where operated according to standard procedures. After this type of operations most often a one week stay at the hospital follows characterized by pain and gastrointestinal problems. Three of the patients received pentobarbital during and after the operations while three of the patients received an infusion of D-myo-inositol-1.2.6-triphosphate ($IP_3$) for three days during and after the operation (2 mg $IP_3$/kg body weight and hour). All the patients were asked to indicate the level of pain as a function of time on a scale between 0 and 100 where 0 represented no pain. The average value over the three-day period following the operation, the pain-index, was calculated for all the patients. The three patients treated with pentabarbital had a pain index of 35 which is in full agreement with data from many other patients treated in a similar way. The three patients treated with $IP_3$ had a pain index of 15 for the same period which demonstrates that $IP_3$ very effectively reduces pain. Furthermore no side-effects or sedative effects could be observed during or after the $IP_3$-treatment.

Example 2

A total of six patients with rheumatoid arthritis were given an infusion of D-myo-inositol-1,2,6-trisphosphate ($IP_3$) for 48 hours (2 mg/kg/hr). The pain experienced by each patient was assessed with a pain score ranging from 0 to 10 where a high figure represents a high sense of pain. The average value was $8.4 \pm 0.8$ before the start of the infusion and after 24 hrs the value was determined to $2.8 \pm 0.9$. This lower value remained not only during the infusion but also for another twelve days after the infusion was stopped.

Thus the results show a quick on-set of the reduction of pain and also a long duration of the analgetic properties after the termination of the administration of the compound.

Example 3

Two groups of rats, 10 animals per group, were used in order to investigate the analgetic effect of D-myo-inositol-1.2.6trisphosphate ($IP_3$). The control group was given an intravenous dose of saline while the other group was given a dose of 5 mg/kg of the sodium salt of $IP_3$. Immediately after intravenous dosing, each rat received an intraperitoneal injection of 1 ml of a 1% (w/w) solution of acetic acid. Directly after that procedure each animal was placed into individual observation chambers and the numbers of writhes elicited during the subsequent 25-minute period were recorded. After the observation period the animals were killed by cervical dislocation. The number of writhes during the observation period is an expression of the pain experienced by the animal. The control group had an average of 48 writhes during the period while the group receiving $IP_3$ had an average of 18 writhes during the period.

The results demonstrate a significant reduction in pain when $IP_3$ is administered.

Example 4

Solution of sodium salt of D-myo-inositol-1.2.6-trisphosphate (IP$_3$) for injection.

0.5 g of the sodium salt of IP$_3$ and 0.77 g NaCl were dissolved in 98.73 ml of water for injection to form a solution for injection into a person or an animal.

I claim:

1. A method of preventing or alleviating pain comprising administering to a human or other mammal in need thereof of a pain preventing or alleviating effective amount of a pharmaceutical composition comprising at least one specific isomer of inositol triphosphate sufficient.

2. A method according to claim 1 wherein said pharmaceutical composition comprises an isomer of inositol triphosphate in salt form.

3. A method according to claim 2 wherein said inositol triphosphate salt is a salt of sodium, potassium, calcium or zinc.

4. A method according to claim 1 wherein said pharmaceutical composition is in a unit dosage form comprising tablets, granules, capsules, solutions or suspensions.

5. A method according to claim 1 wherein said inositol triphosphate is D-myo-inositol-1,2,6-triphosphate.

* * * * *